US010575130B2

(12) United States Patent
Chisaka et al.

(10) Patent No.: US 10,575,130 B2
(45) Date of Patent: Feb. 25, 2020

(54) MOBILE ELECTRONIC DEVICE, CONTROL METHOD, AND RECORDING MEDIUM

(71) Applicant: KYOCERA Corporation, Kyoto-shi, Kyoto (JP)

(72) Inventors: Takumi Chisaka, Yokohama (JP); Shinya Ishizaki, Kawasaki (JP)

(73) Assignee: KYOCERA CORPORATION, Kyoto (JP)

( * ) Notice: Subject to any disclaimer, the term of this patent is extended or adjusted under 35 U.S.C. 154(b) by 62 days.

(21) Appl. No.: 15/754,979

(22) PCT Filed: Aug. 9, 2016

(86) PCT No.: PCT/JP2016/073494
§ 371 (c)(1),
(2) Date: Feb. 23, 2018

(87) PCT Pub. No.: WO2017/033743
PCT Pub. Date: Mar. 2, 2017

(65) Prior Publication Data
US 2019/0239027 A1 Aug. 1, 2019

(30) Foreign Application Priority Data

Aug. 26, 2015 (JP) .................................. 2015-167031

(51) Int. Cl.
*H04W 4/02* (2018.01)
*G01C 5/06* (2006.01)
(Continued)

(52) U.S. Cl.
CPC .............. *H04W 4/026* (2013.01); *G01C 5/06* (2013.01); *G08B 21/02* (2013.01); *G08B 25/08* (2013.01);
(Continued)

(58) Field of Classification Search
CPC ....... G01S 19/14; G01S 19/06; G08B 21/043; G08B 21/0438; G08B 21/0446;
(Continued)

(56) References Cited

U.S. PATENT DOCUMENTS

2013/0339304 A1 12/2013 Lee et al.
2014/0278220 A1* 9/2014 Yuen ...................... G01B 21/16
702/150

(Continued)

FOREIGN PATENT DOCUMENTS

JP 2002-48589 A 2/2002
JP 2013-6474 A 1/2013
(Continued)

OTHER PUBLICATIONS

International Search Report in PCT Application No. PCT/JP2016/073494, dated Nov. 1, 2016, 4pp.

*Primary Examiner* — Daniel Lai
(74) *Attorney, Agent, or Firm* — Hauptman Ham, LLP

(57) ABSTRACT

A mobile electronic device according to one aspect includes a position detector that detects the position of the device; an atmospheric pressure sensor that detects the atmospheric pressure; and a controller that determines a specific state if a decrease in the altitude is detected in accordance with the atmospheric pressure and if the amount of change in the altitude per predetermined time satisfies a determination condition. The controller makes a determination as to whether the device is located within a specific area by using the position detector and changes the determination condition in accordance with a result of the determination.

5 Claims, 9 Drawing Sheets

(51) Int. Cl.
  *G08B 21/02* (2006.01)
  *G08B 25/10* (2006.01)
  *G08B 25/08* (2006.01)
  *H04M 1/00* (2006.01)
  *H04W 4/021* (2018.01)

(52) U.S. Cl.
  CPC .............. *G08B 25/10* (2013.01); *H04M 1/00* (2013.01); *H04W 4/021* (2013.01)

(58) Field of Classification Search
  CPC .............. G08B 21/0453; G08B 25/004; G08B 25/016; G08B 29/16; G08B 29/185; G08B 29/188; G08B 21/22; G08B 21/02; G01C 21/165; G01C 5/06; G01L 2019/0053; G01L 19/12; G01L 5/16; H04W 4/026; H04W 4/021
  See application file for complete search history.

(56) References Cited

U.S. PATENT DOCUMENTS

| | | | | |
|---|---|---|---|---|
| 2015/0025817 | A1* | 1/2015 | Ten Kate | A61B 5/1117 |
| | | | | 702/50 |
| 2015/0192414 | A1* | 7/2015 | Das | G01C 5/06 |
| | | | | 73/384 |
| 2015/0269824 | A1* | 9/2015 | Zhang | G08B 21/0438 |
| | | | | 340/539.12 |

FOREIGN PATENT DOCUMENTS

| | | | | |
|---|---|---|---|---|
| JP | 2013-92923 A | 5/2013 | | |
| JP | 2013-251718 A | 12/2013 | | |
| TW | 201014732 | * 4/2010 | ............. | B60R 21/01 |

* cited by examiner

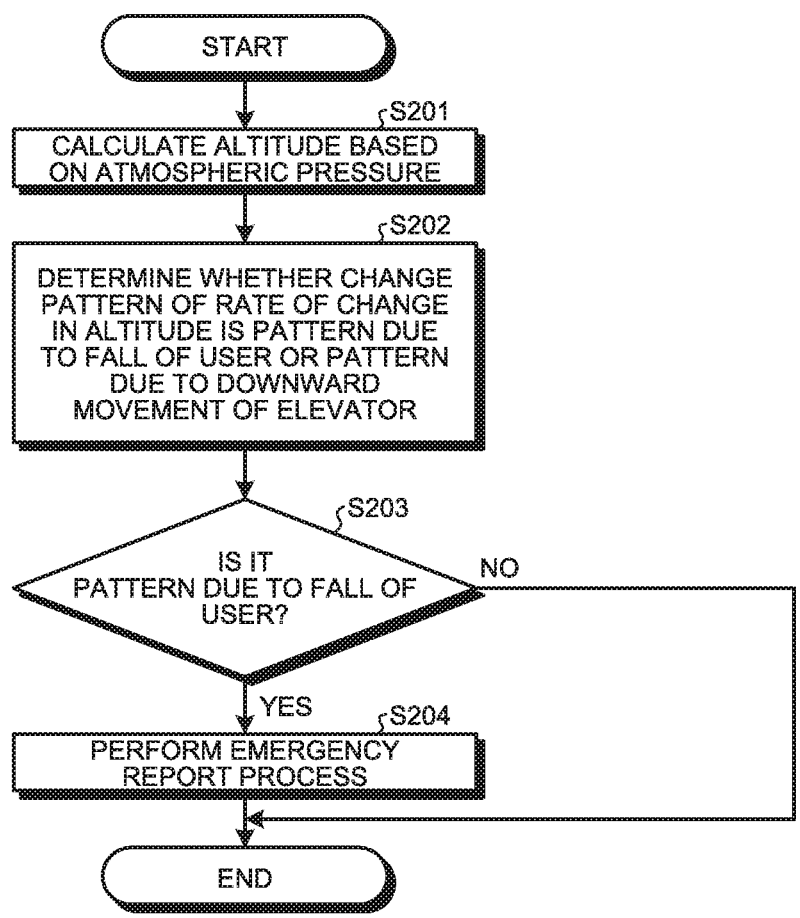

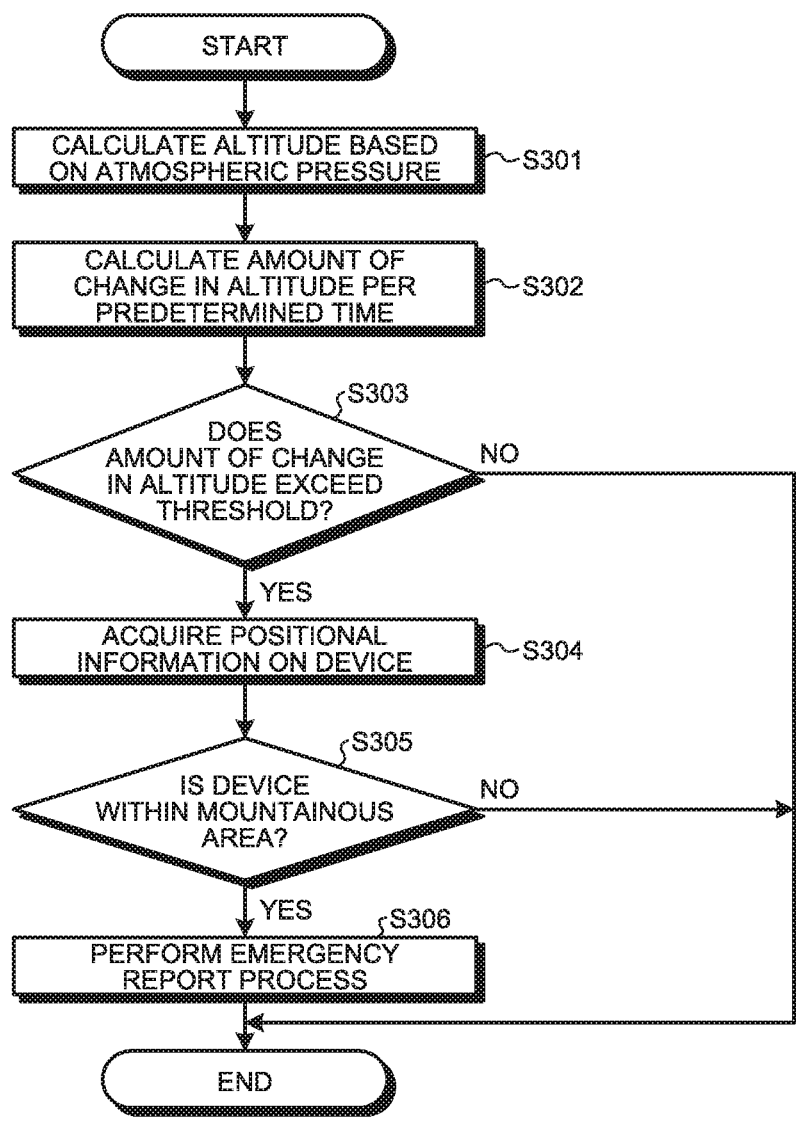

MOBILE ELECTRONIC DEVICE, CONTROL METHOD, AND RECORDING MEDIUM

The present application is a National Phase of International Application No. PCT/JP2016/073494, filed Aug. 9, 2016, and claiming priority under 35 U.S.C. § 119 to Japanese Patent Application No. 2015-167031, filed on Aug. 26, 2015.

The present invention relates to a mobile electronic device, a control method, and a control program.

BACKGROUND

Field

There is a mobile terminal that includes a position detector that detects that the terminal enters a specific area and exits from the specific area; an acceleration sensor (a moving-state detector) that detects a moving state of the terminal; and a notifying unit that notifies the occurrence of a predetermined moving state to outside when the position detector detects an entry to the specific area and the moving state, detected by the acceleration sensor, matches the predetermined moving state.

SUMMARY

A mobile electronic device according to one embodiment includes a position detector that detects a position of the device, an atmospheric pressure sensor that detects an atmospheric pressure, and a controller that determines a specific state if a decrease in an altitude is detected in accordance with the atmospheric pressure and if an amount of change in the altitude per predetermined time satisfies a determination condition. The controller makes a determination as to whether the device is located within a specific area by using the position detector and changes the determination condition in accordance with a result of the determination.

A mobile electronic device according to one embodiment includes an atmospheric pressure sensor that detects an atmospheric pressure, and a controller. The controller determines whether a user has fallen or moved downward by elevator in accordance with a detection pattern of an altitude calculated based on the atmospheric pressure sensor.

A mobile electronic device according to one embodiment includes a position detector that detects a position of the device, an atmospheric pressure sensor that detects an atmospheric pressure, a communication unit, and a controller. The controller determines whether the device is located within a specific area by using the position detector, and if a specific state is obtained in accordance with the atmospheric pressure detected when the device is located within the specific area, starts to communicate with a different device by using the communication unit.

A control method according to one embodiment for a mobile electronic device including a position detector and an atmospheric pressure sensor, includes steps of detecting a position of the device by using the position detector, detecting an atmospheric pressure by using the atmospheric pressure sensor, determining a specific state if a decrease in an altitude is detected in accordance with the atmospheric pressure and if an amount of change in the altitude per predetermined time satisfies a determination condition, and making a determination as to whether the device is located within a specific area by using the position detector and changing the determination condition in accordance with a result of the determination.

A non-transitory computer readable recording medium storing therein a control program according to one embodiment causes a mobile electronic device including a position detector and an atmospheric pressure sensor to execute steps of detecting a position of the device by using the position detector, detecting an atmospheric pressure by using the atmospheric pressure sensor, determining a specific state if a decrease in an altitude is detected in accordance with the atmospheric pressure and if an amount of change in the altitude per predetermined time satisfies a determination condition, and making a determination as to whether the device is located within a specific area by using the position detector and changing the determination condition in accordance with a result of the determination.

BRIEF DESCRIPTION OF THE DRAWINGS

FIG. 10 is a flowchart that illustrates the steps of the process for an example of the smartphone's different control related to the time of fall.

FIG. 11 is a flowchart that illustrates the steps of the process for an example of the smartphone's different control related to the time of fall.

DETAILED DESCRIPTION

Embodiments for implementing a mobile electronic device, a control method, and a control program according to the present application are explained in detail with reference to the drawings. As an example of the mobile electronic device, a smartphone is explained below.

Embodiments

Figure 1:
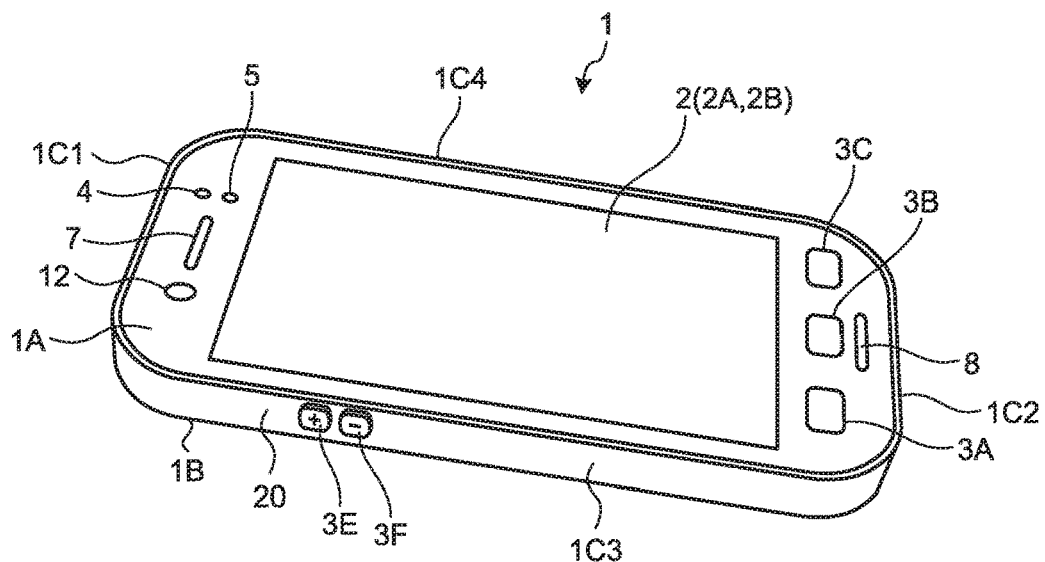
FIG. 1 is a perspective view of a smartphone according to embodiments.
Figure 2:
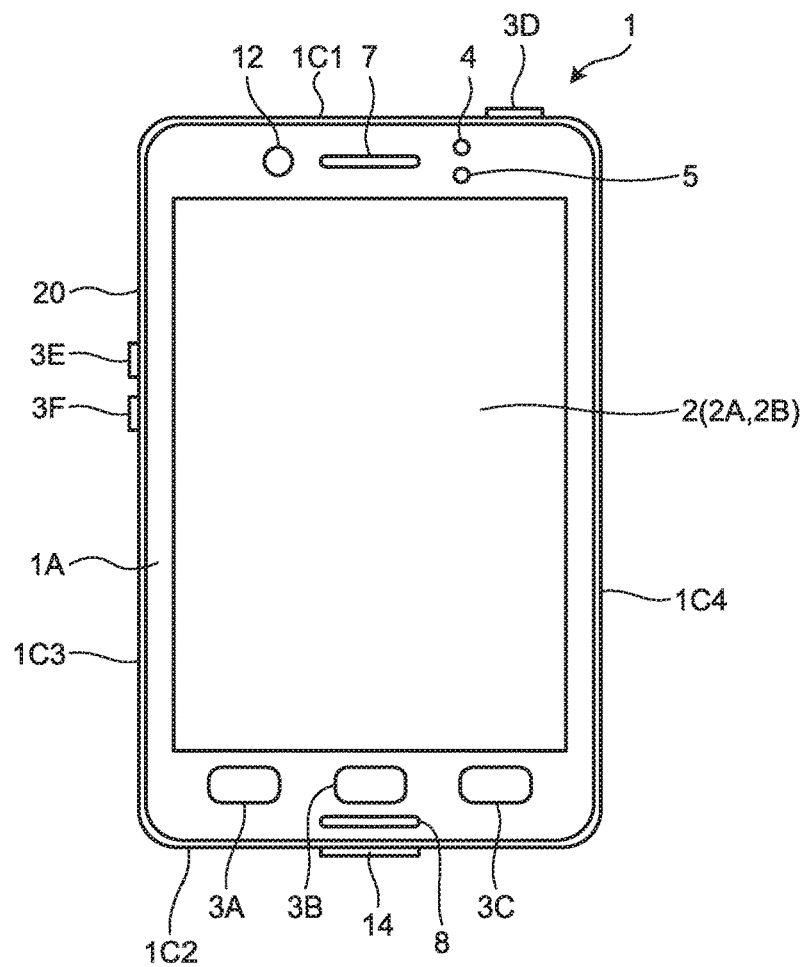
FIG. 2 is a front view of the smartphone.
Figure 3:
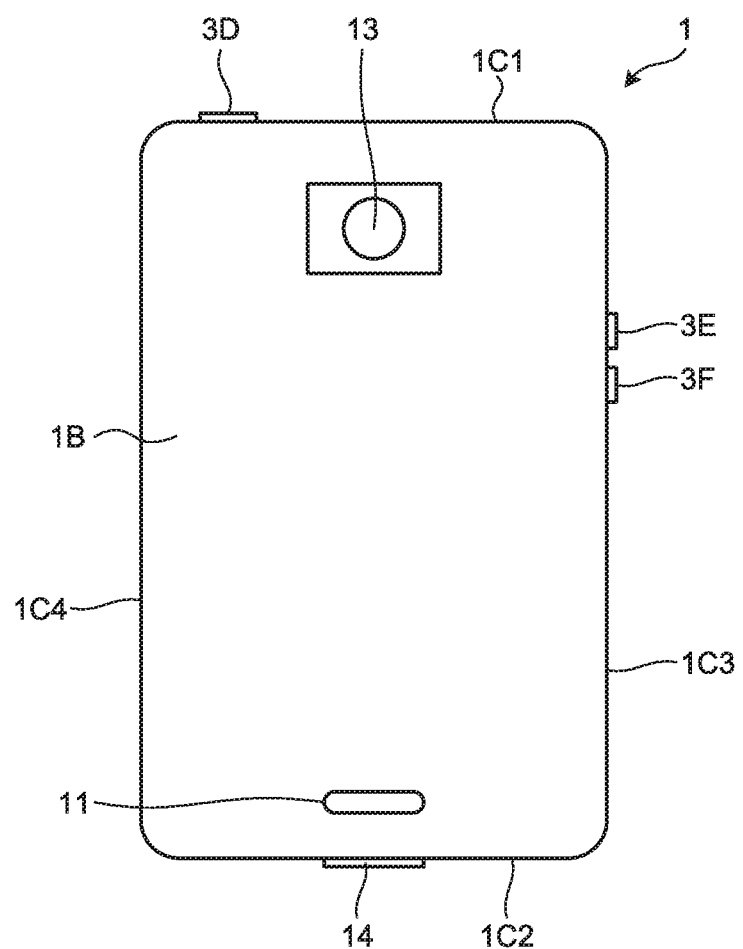
FIG. 3 is a back view of the smartphone.

Conventional mobile terminals may have room for improvements in the technology for determining the occurrence of a predetermined state. With reference to FIG. 1 to FIG. 3, the overall configuration of a smartphone 1 according to embodiments is explained. As illustrated in FIG. 1 to FIG. 3, the smartphone 1 includes a housing 20. The housing 20 includes a front face 1A, a back face 1B, and side faces 1C1 to 1C4. The front face 1A is the front face of the housing 20. The back face 1B is the back face of the housing 20. The side faces 1C1 to 1C4 are the side faces that connect the front face 1A and the back face 1B. Hereafter, the side faces 1C1 to 1C4 are sometimes collectively referred to as a side face 1C without specifying each face.

A touch screen display 2, buttons (keys) 3A to 3C, an illuminance sensor 4, a proximity sensor 5, a receiver 7, a microphone 8, and a camera 12 are provided on the front face 1A of the smartphone 1. A speaker 11 and a camera 13 are provided on the back face 1B of the smartphone 1. Buttons 3D to 3F and a connector 14 are provided on the side face 1C of the smartphone 1. Hereafter, the buttons 3A to 3F are sometimes collectively referred to as a button 3 without specifying each button.

The touch screen display 2 includes a display 2A and a touch screen 2B. According to the example in FIG. 1, each of the display 2A and the touch screen 2B is substantially rectangular in shape; however, the shapes of the display 2A and the touch screen 2B are not limited thereto. Each of the display 2A and the touch screen 2B may have any shape, such as a square or a circle. According to the example in FIG. 1, the display 2A and the touch screen 2B are located in an overlapped manner; however, the positions of the display 2A and the touch screen 2B are not limited thereto. For example, the display 2A and the touch screen 2B may be located side by side or located apart from each other. According to the example in FIG. 1, the long side of the display 2A is arranged along the long side of the touch screen 2B, and the short side of the display 2A is arranged along the short side of the touch screen 2B; however, the way of overlapping the display 2A and the touch screen 2B is not limited thereto. If the display 2A and the touch screen 2B are located in an overlapped manner, for example, one or more sides of the display 2A do not need to be arranged along any side of the touch screen 2B.

The display 2A includes a display device, such as a liquid crystal display (LCD: Liquid Crystal Display), an organic EL display (OELD: Organic Electro-Luminescence Display), or an inorganic EL display (IELD: Inorganic Electro-Luminescence Display). The display 2A presents texts, images, symbols, graphics, and the like.

The touch screen 2B detects contact with the touch screen 2B by using a finger, pen, stylus pen, or the like. The touch screen 2B may detect the positions of contact with the touch screen 2B by using multiple fingers, pens, stylus pens, or the like. In the following explanations, the finger, pen, stylus pen, or the like, which is in contact with the touch screen 2B, is sometimes referred to as a "contact object" or "contact substance".

The detection system of the touch screen 2B may be any system, such as a capacitive system, a resistive layer system, a surface acoustic wave system (or an ultrasonic system), an infrared system, an electromagnetic induction system, or a load sensing system. In the following explanations, for ease of explanation, it is assumed that the user touches the touch screen 2B by using a finger to operate the smartphone 1.

The smartphone 1 determines the type of gesture on the basis of at least one of the contact that is detected by the touch screen 2B, the position where the contact is detected, a change in the position where the contact is detected, the interval of detected contacts, and the number of times the contact is detected. The gesture is an operation that is performed on the touch screen 2B. Examples of the gesture determined by the smartphone 1 include, but are not limited to, touch, long touch, release, swipe, tap, double tap, long tap, drag, flick, pinch-in, and pinch-out.

The smartphone 1 performs operations in accordance with the gestures that are determined through the touch screen 2B. Thus, the operability that is intuitive and easy-to-use for users may be achieved. The operation that is performed by the smartphone 1 in accordance with the determined gesture is sometimes different depending on the screen that is presented on the display 2A. In the following explanations, for ease of explanation, "the touch screen 2B detects the contact and the smartphone 1 determines that the type of gesture is X on the basis of the detected contact" is sometimes described as "the smartphone detects X" or "the controller detects X".

Figure 4:
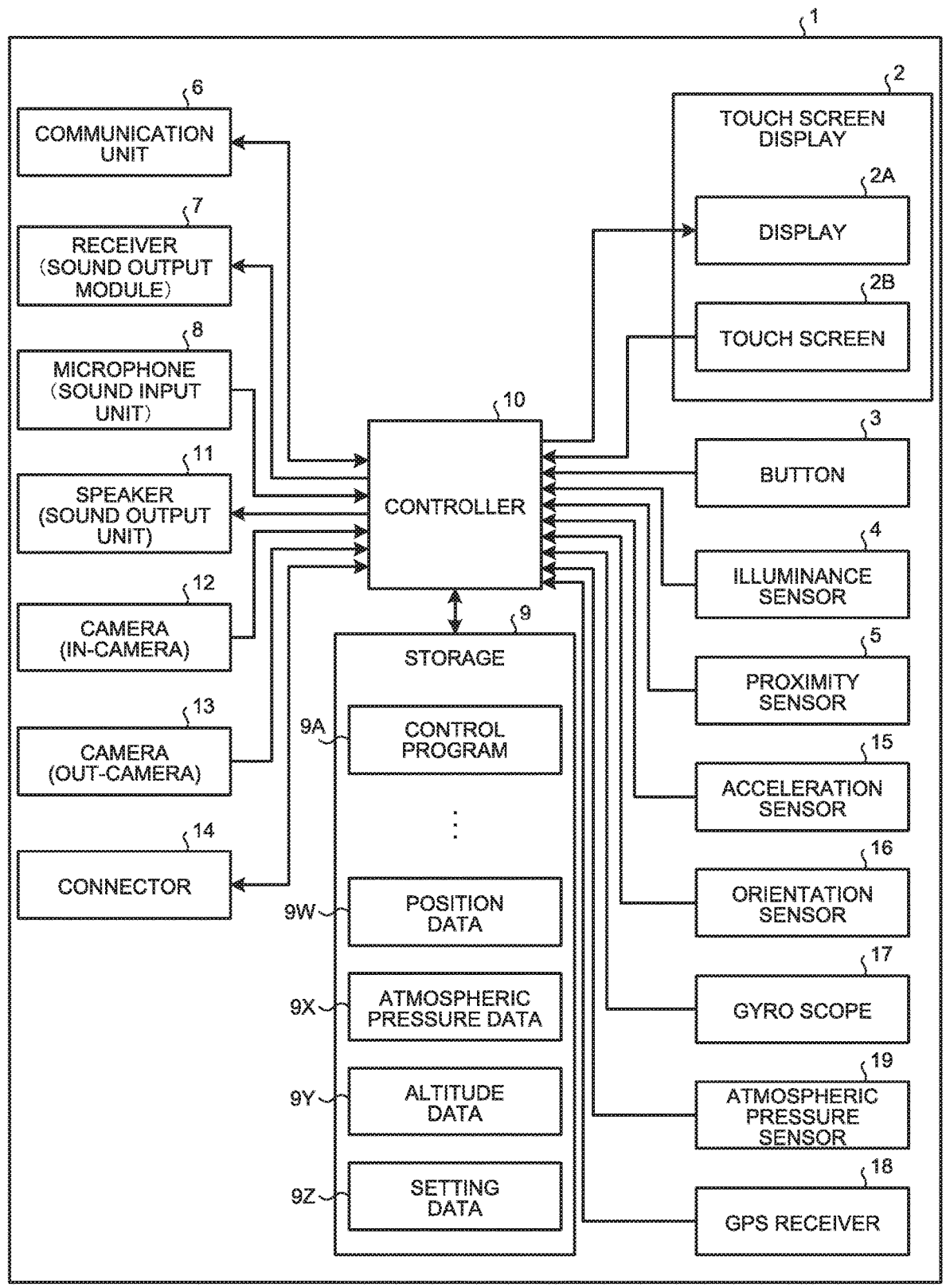
FIG. 4 is a block diagram of the smartphone.

FIG. 4 is a block diagram of the smartphone 1. The smartphone 1 includes the touch screen display 2, the button 3, the illuminance sensor 4, the proximity sensor 5, a communication unit 6, the receiver 7, the microphone 8, a storage 9, a controller 10, the speaker 11, the cameras 12 and 13, the connector 14, an acceleration sensor 15, an orientation sensor 16, a gyro scope 17, a GPS (Global Positioning System) receiver 18, and an atmospheric pressure sensor 19.

As described above, the touch screen display 2 includes the display 2A and the touch screen 2B. The display 2A presents texts, images, symbols, graphics, or the like. The touch screen 2B detects contact. The controller 10 detects a gesture on the smartphone 1. Specifically, the controller 10 detects an operation (gesture) on the touch screen 2B (the touch screen display 2) in cooperation with the touch screen 2B.

The button 3 is operated by a user. The button 3 includes the button 3A to the button 3F. The controller 10 detects an operation on the button 3 in cooperation with the button 3. Examples of the operation on the button 3 include, but are not limited to, click, double click, triple click, push, and multi-push.

The buttons 3A to 3C are, for example, the home button, the back button, or the menu button. The button 3D is, for example, the power on/off button of the smartphone 1. The button 3D may double as a sleep/sleep-cancel button. The buttons 3E and 3F are, for example, the sound volume buttons.

The illuminance sensor 4 detects the illuminance of the surrounding light of the smartphone 1. The illuminance is the value of the light flux that enters a unit area of the measurement surface of the illuminance sensor 4. The illuminance sensor 4 is, for example, used to adjust the brightness of the display 2A. The proximity sensor 5 detects the presence of an object in the neighborhood in a non-contact manner. The proximity sensor 5 detects the presence of an object on the basis of a change in the magnetic field, a change in the return time of a reflected wave of an ultrasonic wave, or the like. The proximity sensor 5 detects that, for example, the touch screen display 2 is brought close to the face. The illuminance sensor 4 and the proximity sensor 5 may be configured as a single sensor. The illuminance sensor 4 may be used as a proximity sensor.

The communication unit 6 performs communication via radio waves. The communication system, supported by the communication unit 6, is a radio communication standard. Examples of the radio communication standard include, but are not limited to, the communication standard for cellular phones, such as 2G, 3G, or 4G. Examples of the communication standard for cellular phones include, but are not limited to, LTE (Long Term Evolution), W-CDMA (Wideband Code Division Multiple Access), CDMA2000 (Wideband Code Division Multiple Access 2000), PDC (Personal Digital Cellular), GSM (registered trademark) (Global System for Mobile Communications), and PHS (Personal Handy-phone System). Furthermore, examples of the radio communication standard include, but are not limited to, WiMAX (registered trademark) (Worldwide Interoperability for Microwave Access), IEEE802.11, Bluetooth (registered trademark), IrDA (Infrared Data Association), and NFC (Near Field Communication). The communication unit 6 may support one or more out of the above-described communication standards.

The receiver 7 and the speaker 11 are one example of an output unit that outputs sound. The receiver 7 and the speaker 11 may output sound signals, transmitted from the controller 10, as sounds. The receiver 7 may be, for example, used to output the voice of the other person during a telephone call. The speaker 11 may be, for example, used to output the ring tone and music. One of the receiver 7 and the speaker 11 may double as the function of the other. The microphone 8 is an example of an input module that inputs sound. The microphone 8 converts the voice of the user, or the like, into sound signals and transmits them to the controller 10.

The storage 9 may store programs and data. The storage 9 may be also used as a work area that temporarily stores processing results of the controller 10. The storage 9 includes a recording medium. The recording medium may include any non-transitory (non-transitory) storage medium, such as a semiconductor storage medium or a magnetic storage medium. The storage 9 may include multiple types of storage media. The storage 9 may include the combination of a portable storage medium, such as a memory card, an optical disk, or a magnetic optical disk, and a reading device for the storage medium. The storage 9 may include a storage device that is used as a temporary memory area, such as a RAM (Random Access Memory).

The programs stored in the storage 9 include an application executed in the foreground or the background and a control program that supports execution of the application. For example, the application causes the display 2A to present the screen and causes the controller 10 to perform the operation that corresponds to the gesture that is detected through the touch screen 2B. The control program is, for example, the OS. The application and the control program may be installed in the storage 9 through a wireless communication by the communication unit 6 or through a non-transitory storage medium.

The storage 9 stores for example a control program 9A, position data 9W, atmospheric pressure data 9X, altitude data 9Y, and setting data 9Z. The position data 9W includes the positional information that indicates the position of the smartphone 1. The atmospheric pressure data 9X includes the information that indicates the atmospheric pressure that acts on the smartphone 1. The altitude data 9Y includes the information that indicates the altitude of the smartphone 1. The setting data 9Z includes the information related to various settings with regard to operations of the smartphone 1.

The control program 9A may provide functions related to various controls for operating the smartphone 1. The control program 9A controls, for example, the communication unit 6, the receiver 7, the microphone 8, and the like, to make a telephone call. The functions provided by the control program 9A include the functions that perform various controls, such as changing the information presented on the display 2A, in accordance with the gesture that is detected via the touch screen 2B. The functions provided by the control program 9A include the function to calculate the altitude by controlling the atmospheric pressure sensor 19. The function provided by the control program 9A may be used in combination with the function that is provided by a different program.

The control program 9A may provide the function to determine the state of the smartphone 1 (the device) in accordance with the atmospheric pressure detected by the atmospheric pressure sensor 19. The state of the device includes, for example, a state where a user who carries the device has fallen. The state of the device includes, for example, a moving state by using an elevator. The method for determining the state of the device is described later. The control program 9A may provide the function to make an emergency report on the occurrence of a falling state. The control program 9A may provide the function to determine whether the smartphone 1 is within a specific area on the basis of the present location detected by the GPS receiver 18. Examples of the specific area include, but are not limited to, a mountainous area, an urban area, and an area where there are no buildings with an elevator.

A mountainous area may be appropriately set, for example, by referring to mountainous areas that are defined by an authority, such as Geospatial Information Authority of Japan. An urban area may be appropriately set, for example, on the basis of the information related to the city, such as the density of population. An area where there are no buildings with an elevator may be appropriately set, for example, on the basis of the information with regard to the presence or absence of tall buildings.

In the position data 9W, positional information may be stored in chronological order. Examples of the positional information include, but are not limited to, items such as the latitude, the longitude, and the time. The latitude and the longitude indicate the present location detected by the GPS receiver 18. The time indicates the time when the GPS receiver 18 detects the present location. If the GPS receiver 18 detects the present location at predetermined timing, the positional information that indicates the present location is added to the position data 9W. Examples of the predetermined timing include, but are not limited to, when a sampling time comes, and when a request to detect the present location is made. For example, in some cases, it is difficult to obtain a result if measurement of the positional information is started at a timing such that the detected altitude has changed or is changing. For this reason, it is more preferable that positional information is acquired on a regular basis and is stored in the position data 9W.

In the atmospheric pressure data 9X, atmospheric pressure information may be stored in chronological order. Examples of the atmospheric pressure information include, but are not limited to, items such as the time, the value of the atmospheric pressure, and an amount of change in the atmospheric pressure. The time indicates the time when the atmospheric pressure sensor 19 detects the atmospheric pressure. The value of the atmospheric pressure indicates the value of the atmospheric pressure detected by the atmospheric pressure sensor 19. The amount of change in the atmospheric pressure indicates the amount of change in the atmospheric pressure per unit time, detected by the atmospheric pressure sensor 19.

In the altitude data 9Y, altitude information may be stored in chronological order. Examples of the altitude information include, but are not limited to, items such as the time, the value of the altitude, and the amount of change in the altitude. The time indicates the time when the altitude is detected (calculated). The value of the altitude indicates the value of the altitude calculated in accordance with the value of the atmospheric pressure. The amount of change in the altitude indicates the amount of change in the calculated altitude per unit time.

The setting data 9Z includes determination condition data for making determination with regard to a fall of a user. The determination condition data includes a condition for determining whether a change in the altitude is caused by a fall or a downward movement of an elevator. Examples of the determination condition include, but are not limited to, a first threshold and a second threshold. The first threshold may be a threshold for determining whether a change in the altitude is caused by a fall. The second threshold may be a threshold for determining whether a change in the altitude is caused by a downward movement of an elevator. Typically, with regard to the amount of change in the altitude per predetermined time, the amount of change in the altitude due to a fall is larger than the amount of change in the altitude due to a downward movement of an elevator.

In embodiments, an explanation is given of a case where the determination condition data includes the thresholds; however, the embodiments are not limited thereto. The determination condition data may include, for example, a pattern of changes in the altitude due to a fall. The determination condition data may include, for example, a pattern of changes in the altitude due to a downward movement of an elevator.

The setting data 9Z includes the area data for determining a predetermined area. The area data may indicate, for example, an area at the position that corresponds to a mountainous area. The area data may indicate, for example, an area at the position that corresponds to an urban area. The area data may indicate, for example, the position of a building with an elevator. The area data may include, for example, data that corresponds to multiple areas.

The controller 10 is an arithmetic processing device. Examples of the arithmetic processing device include, but are not limited to, a CPU (Central Processing Unit), a SoC (System-on-a-chip), an MCU (Micro Control Unit), a FPGA (Field-Programmable Gate Array), and a coprocessor. The controller 10 may integrally control operations of the smartphone 1 in cooperation with various devices. Various functions of the controller 10 may be implemented in accordance with the control of the controller 10.

Specifically, the controller 10 may execute commands included in programs that are stored in the storage 9. The controller 10 may refer to the data that is stored in the storage 9 as needed. The controller 10 controls functional units in accordance with data and commands. The controller 10 controls functional units to implement various functions. Examples of the functional unit include, but are not limited to, the display 2A, the communication unit 6, the receiver 7, and the speaker 11. The controller 10 sometimes changes control in accordance with a detection result of a detection unit. Examples of the detection unit include, but are not limited to, the touch screen 2B, the button 3, the illuminance sensor 4, the proximity sensor 5, the microphone 8, the camera 12, the camera 13, the acceleration sensor 15, the orientation sensor 16, the gyro scope 17, the GPS receiver 18, and the atmospheric pressure sensor 19.

The controller 10 executes, for example, the control program 9A so as to perform various types of control, such as changing the information that is presented on the display 2A, in accordance with the gesture that is detected via the touch screen 2B.

The camera 12 is an in-camera that takes an image of the object that is opposed to the front face 1A. The camera 13 is an out-camera that takes an image of the object that is opposed to the back face 1B.

The connector 14 is a terminal that is connected to a different device. The connector 14 may be a general-purpose terminal, such as a USB (Universal Serial Bus), HDMI (registered trademark) (High-Definition Multimedia Interface), Light Peak (Thunderbolt (registered trademark)), or an earphone microphone connector. The connector 14 may be a dedicated terminal, such as a Dock connector. Examples of the device that is connected to the connector 14 include, but are not limited to, an external storage, a speaker, and a communication device.

The acceleration sensor 15 may detect the direction and the level of acceleration that acts on the smartphone 1. The orientation sensor 16 may detect the direction of the earth magnetism. The gyro scope 17 may detect the angle and the angular velocity of the smartphone 1. The GPS receiver 18 may detect the present location of the smartphone 1. The atmospheric pressure sensor 19 may detect the atmospheric pressure that acts on the smartphone 1. Detection results of the acceleration sensor 15, the orientation sensor 16, the gyro scope 17, and the atmospheric pressure sensor 19 are used in combination to detect changes in the position and the attitude of the smartphone 1.

In embodiments, an explanation is given of a case where the smartphone 1 includes the GPS receiver 18; however, the embodiments are not limited thereto. For example, the smartphone 1 may detect the present location on the basis of the base station of which the communication unit 6 uses radio communication. For example, the smartphone 1 may use multiple systems to detect the present location.

All or some of the programs and data, stored in the storage 9 in FIG. 4, may be downloaded from a different device through a wireless communication by the communication unit 6. All or some of the programs and data, stored in the storage 9 in FIG. 4, may be stored in a non-transitory storage medium that is readable by a reading device included in the storage 9. All or some of the programs and data, stored in the storage 9 in FIG. 4, may be stored in a non-transitory storage medium that is readable by a reading device that is connected to the connector 14. Examples of the non-transitory storage medium include, but are not limited to, an optical disk, such as CD (registered trademark), DVD (registered trademark), or Blu-ray (registered trademark), a magnetic optical disk, a magnetic storage medium, a memory card, and a solid-state storage medium.

The configuration of the smartphone 1, illustrated in FIG. 4, is an example, and modifications may be appropriately made to such a degree that the scope of the present application is not degraded. For example, the number and the type of the buttons 3 are not limited to the example in FIG. 4. As the buttons for operations related to the screen, the smartphone 1 may include buttons in the numeric keypad arrangement, QWERTY arrangement, or the like, instead of the buttons 3A to 3C. The smartphone 1 may include only one button or include no buttons for operations related to the screen. In the example that is illustrated in FIG. 4, the smartphone 1 includes two cameras; however, the smartphone 1 may include only one camera or may include no cameras. In the example that is illustrated in FIG. 4, the smartphone 1 includes four types of sensors to detect the position and the attitude; however, the smartphone 1 does not need to include any of the sensors. Alternatively, the smartphone 1 may include a different type of sensor to detect at least one of the position and the attitude.

An explanation is given of an example of the control related to detection of altitude changes by the smartphone 1. The smartphone 1 executes the control program 9A so as to calculate the altitude on the basis of the detected atmospheric pressure. When the atmospheric pressure sensor 19 detects the atmospheric pressure, the smartphone 1 applies the atmospheric pressure to an altitude calculus equation to calculate the altitude. The altitude calculus equation is a calculus equation to calculate the altitude from the atmospheric pressure. The smartphone 1 stores the altitude information, which indicates the calculated altitude, in the altitude data 9Y of the storage 9.

Figure 5:
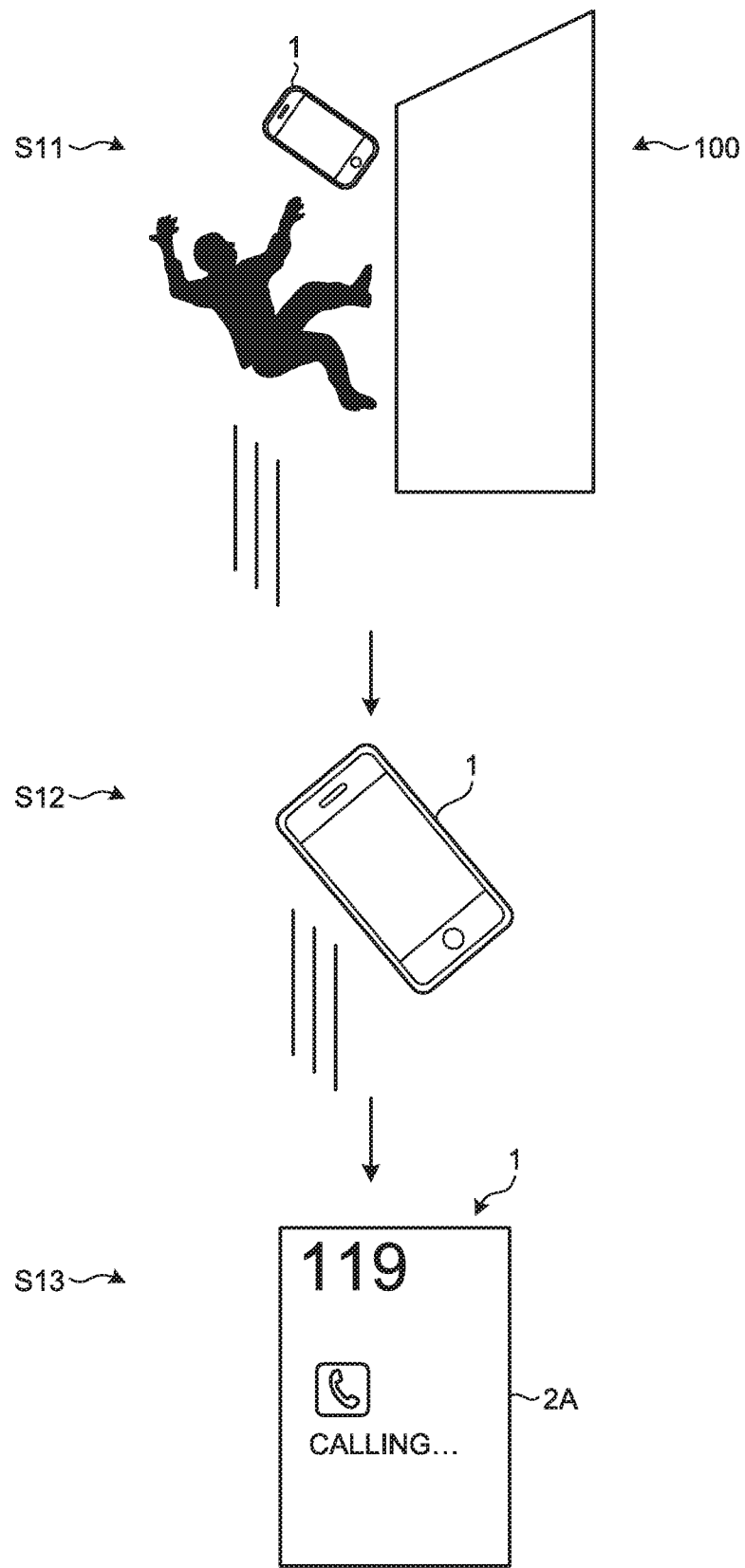
FIG. 5 is a diagram that illustrates an example of the smartphone's control related to the time of fall.
Figure 6:
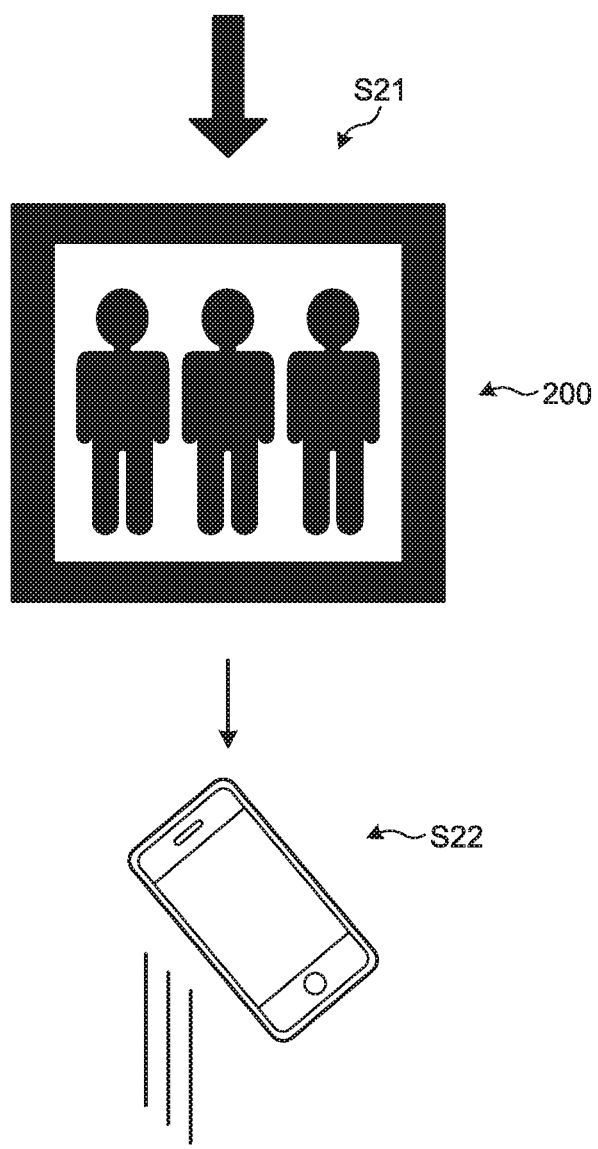
FIG. 6 is a diagram that illustrates an example of the smartphone's control related to the time of downward movement of an elevator.

With reference to FIG. 5 and FIG. 6, an explanation is given of the smartphone 1's control related to the time of a decrease in the altitude. FIG. 5 is a diagram that illustrates an example of the smartphone 1's control related to the time of fall. FIG. 6 is a diagram that illustrates an example of the smartphone 1's control related to the time of downward movement of an elevator. In the following explanation, the same components are attached with the same reference numerals, and duplicated explanations are sometimes omitted.

In the example illustrated in FIG. 5, a user is located in a mountainous area 100 while carrying the smartphone 1. The smartphone 1 detects the atmospheric pressure at predetermined time intervals by using the atmospheric pressure sensor 19 and stores it in the atmospheric pressure data 9X. At Step S11, the smartphone 1 determines whether the present location detected by the GPS receiver 18 is within the mountainous area 100. When it is determined that it is within the mountainous area 100, the smartphone 1 changes the threshold, which is a determination condition, into the first threshold that corresponds to the mountainous area 100. The smartphone 1 determines whether the amount of change in the altitude exceeds the first threshold.

At Step S11, for example, the user has encountered a fall accident during mountain climbing. Examples of the fall accident include, but are not limited to, accidents such as fall, tumble, or slip drop. The smartphone 1 has an altitude rapidly decreasing as it falls in a state where it is held by the user or in a state where it is not held. In this case, at Step S12, when it is detected that the altitude decreases in accordance with the detected atmospheric pressure, the smartphone 1 determines that the amount of change in the altitude per predetermined time exceeds the first threshold. That is, the smartphone 1 determines that a state is such that the user has encountered a fall accident.

When it is detected that the altitude decreases and when it is determined that it is a state where a fall accident has occurred, the smartphone 1 starts to communicate with a predetermined different device by using the communication unit 6 at Step S13. In the example illustrated in FIG. 5, the smartphone 1 automatically makes an emergency report. The emergency report includes, for example, setting a state for enabling calling to a person on the other side. The emergency report includes, for example, report of the occurrence of a fall accident, or the like, to an official organization.

In the example illustrated in FIG. 6, the user is located in an urban area 200 while carrying the smartphone 1. The smartphone 1 detects the atmospheric pressure at predetermined time intervals by using the atmospheric pressure sensor 19 and stores it in the atmospheric pressure data 9X. At Step S21, the smartphone 1 determines whether the present location detected by the GPS receiver 18 is within the mountainous area 100. When it is determined that it is not within the mountainous area 100, the smartphone 1 changes the threshold, which is a determination condition, into the second threshold that corresponds to the urban area 200. The smartphone 1 determines whether the amount of change in the altitude exceeds the second threshold. The second threshold is a larger threshold than the first threshold. Specifically, the second threshold is such a value that, for example, it is not reached by the amount of change in the altitude per predetermined time due to a downward movement of the elevator but it is reached by a decrease in the altitude due to a fall.

At Step S21, the user is moving downward by the elevator that is within the urban area 200 while carrying the smartphone 1. The smartphone 1 has an altitude gradually decreasing as it is moved downward by elevator. Alternatively, the smartphone 1 has an altitude not decreasing if it is moved downward by elevator by few floors. That is, a change in the altitude due to a downward movement of the elevator is smaller than a change in the altitude due to a fall. In this case, at Step S22, the smartphone 1 determines that the amount of change in the altitude does not exceed the second threshold. If the amount of change in the altitude does not exceed the second threshold, the smartphone 1 determines that it is a state where the user has not encountered a fall accident.

When it is detected that the altitude decreases and when it is determined that it is a state where no fall accident occurs, the smartphone 1 does not make any emergency report but continuously detects altitude changes.

In this way, the smartphone 1 may specify an area on the basis of the detected present location of the device and change the determination condition for the amount of change in the altitude in accordance with the area. As a result, the smartphone 1 may improve the determination accuracy as to whether it is a decrease in the altitude due to a fall or a decrease in the altitude due to a downward movement of an elevator. When it is determined that it is a decrease in the altitude due to a fall, the smartphone 1 may automatically make an emergency report. Thus, because of automatic emergency reports in response to detection of a fall, the smartphone 1 may contribute to an improvement in the probability of living of persons in the accident and reduction of missing persons. The smartphone 1 may prevent emergency reports from being mistakenly made when a decrease in the altitude occurs due to a downward movement of the elevator.

Figure 7:
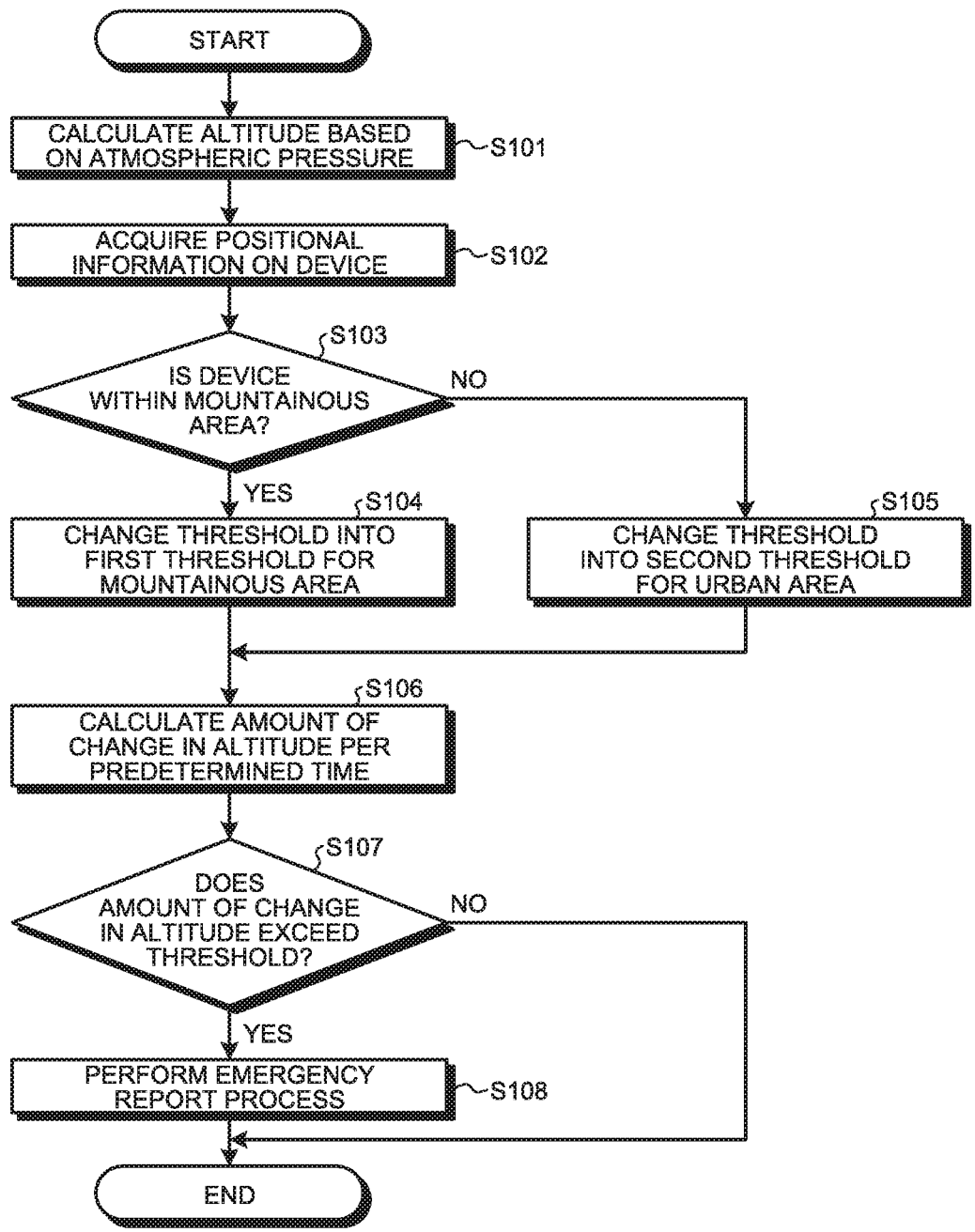
FIG. 7 is a flowchart that illustrates the steps of the process for an example of the smartphone's control related to the time of fall.

With reference to FIG. 7, an explanation is given of the steps of the process for the smartphone 1's control related to the time of fall. FIG. 7 is a flowchart that illustrates the steps of the process for an example of the smartphone 1's control related to the time of fall. The steps of the process illustrated in FIG. 7 are performed when the controller 10 executes the control program 9A. The steps of the process illustrated in FIG. 7 are repeatedly performed.

As illustrated in FIG. 7, at Step S101, the controller 10 of the smartphone 1 calculates the altitude based on the atmospheric pressure. For example, the controller 10 applies the atmospheric pressure in the atmospheric pressure data 9X, detected by the atmospheric pressure sensor 19, to the altitude calculus equation to calculate the altitude and stores the calculation result in the altitude data 9Y of the storage 9.

At Step S102, the controller 10 acquires the positional information on the device. For example, the controller 10 acquires the latest positional information from the positional information stored in the position data 9W. The controller 10 may cause the GPS receiver 18 to detect the positional information so as to acquire the detected positional information.

At Step S103, the controller 10 determines whether the device is within the mountainous area 100. For example, the controller 10 determines that the device is within the mountainous area 100 if the present location of the device is within the area at the position that corresponds to the mountainous area 100.

If it is determined that the device is within the mountainous area 100 (Step S103, Yes), the controller 10 proceeds to Step S104. At Step S104, the controller 10 changes the threshold, which is a determination condition, into the first threshold for the mountainous area 100. When a change to the determination condition is complete, the controller 10 proceeds to Step S106 that is described later.

If it is determined that the device is not within the mountainous area 100 (Step S103, No), the controller 10 proceeds to Step S105. At Step S105, the controller 10 changes the threshold, which is a determination condition, into the second threshold for the urban area 200. When a change to the determination condition is complete, the controller 10 proceeds to Step S106.

At Step S106, the controller 10 calculates the amount of change in the altitude per predetermined time from the altitude data 9Y and stores the calculation result in the storage 9. At Step S107, the controller 10 determines whether the amount of change in the altitude exceeds the threshold. If it is determined that the amount of change in the altitude does not exceed the threshold (Step S107, No), the controller 10 terminates the steps of the process illustrated in FIG. 7.

If it is determined that the amount of change in the altitude exceeds the threshold (Step S107, Yes), the controller 10 proceeds to Step S108. At Step S108, the controller 10 performs an emergency report process. For example, the controller 10 performs an emergency report process so as to make a phone call to a specific phone number via the communication unit 6. When the emergency report process is complete, the controller 10 terminates the steps of the process illustrated in FIG. 7.

According to embodiments, the emergency report process may be, for example, a process performed by the controller 10 to transmit an e-mail to a specific e-mail address. The e-mail may include, for example, a message that indicates the occurrence of a fall accident, or the like. The e-mail may include, for example, the information on the position where a fall accident has occurred. The emergency report process may be, for example, a process to generate rescue signals, or the like, each time a predetermined time elapses.

Embodiments disclosed in the present application may be modified without departing from the spirit and the scope of the present application. Furthermore, embodiments disclosed in the present application may be combined as appropriate. For example, embodiments may be modified as described below.

For example, each program illustrated in FIG. 4 may be divided into multiple modules or combined with other programs.

An explanation is given below of the smartphone 1 according to another example of embodiments. The smartphone 1 according to another example of embodiments has the same configuration as that of the smartphone 1 illustrated in FIG. 1 to FIG. 4 except that the function of the control program 9A is different. Therefore, another example of embodiments is explained below by using the smartphone 1 as an example.

Figure 8:
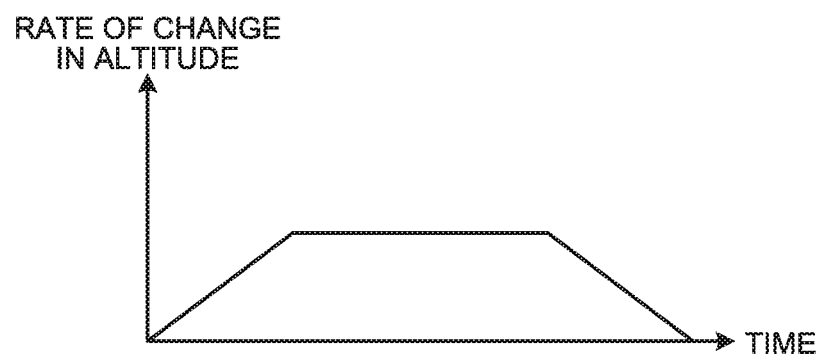
FIG. 8 is a graph that illustrates the relationship between the rate of change in the altitude due to an elevator and the time.
Figure 9:
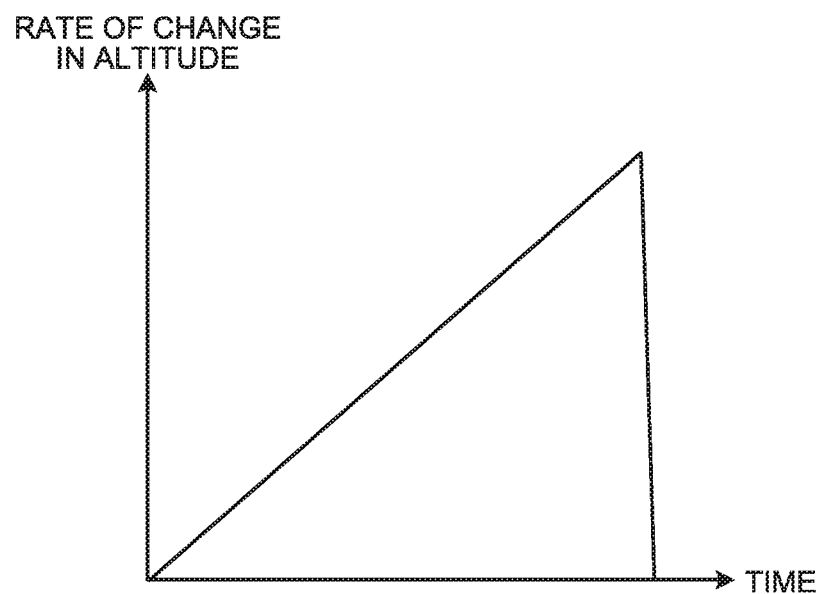
FIG. 9 is a graph that illustrates the relationship between the rate of change in the altitude due to a fall and the time.

With reference to FIG. 8 and FIG. 9, an explanation is given of another example where the smartphone 1 determines a decrease in the altitude. FIG. 8 is a graph that illustrates the relationship between the rate of change in the altitude due to an elevator and the time. FIG. 9 is a graph that illustrates the relationship between the rate of change in the altitude due to a fall and the time. In FIG. 8 and FIG. 9, the vertical axis represents the rate of change in the altitude. The horizontal axis represents the time. The rate of change in the altitude is the amount of change in the altitude per unit time with regard to the altitude calculated by the smartphone 1.

As illustrated in FIG. 8, if the elevator starts to move downward, the smartphone 1 may detect a state where the rate of change in the altitude is increasing. For example, if the speed of downward movement of the elevator is stable, the smartphone 1 may detect a state where the rate of change in the altitude is stable. For example, if the speed of downward movement decreases in accordance with the elevator stopped, the smartphone 1 may detect a state where the rate of change in the altitude decreases to reach zero.

As illustrated in FIG. 9, in the case of a fall from a height, the smartphone 1 may detect a state where the rate of change in the altitude is continuously increasing. This is an increase larger than an increase in a case where the elevator starts to move downward. For example, if the amount of change in the altitude is zero after landing, the smartphone 1 may detect a state where the rate of change in the altitude becomes zero after increasing.

The pattern of the rate of change in the altitude is likely to be a pattern of the rate of change in the altitude due to a fall if there is no time period during which the rate of change is stable after it is gradually increased. For example, the smartphone 1 may store a detection pattern of the rate of change in the altitude due to a fall of the user as a determination condition in the storage 9. For example, the smartphone 1 may store a detection pattern of the rate of change in the altitude due to a downward movement of the elevator as a determination condition in the storage 9. The method for determining a pattern includes, for example, a method of extracting a characteristic pattern that is after the rate of change in the altitude starts to change and making a determination based on whether the pattern matches the detection pattern, which is a determination condition.

With reference to FIG. 10, an explanation is given of the steps of the process for the smartphone 1's different control related to the time of fall. FIG. 10 is a flowchart that illustrates the steps of the process for an example of the smartphone 1's different control related to the time of fall. The steps of the process illustrated in FIG. 10 are performed when the controller 10 executes the control program 9A. The steps of the process illustrated in FIG. 10 are repeatedly performed.

As illustrated in FIG. 10, at Step S201, the controller 10 of the smartphone 1 calculates the altitude based on the atmospheric pressure. For example, the controller 10 applies the atmospheric pressure in the atmospheric pressure data 9X, detected by the atmospheric pressure sensor 19, to the altitude calculus equation to calculate the altitude and stores the calculation result in the altitude data 9Y of the storage 9.

At Step S202, on the basis of the altitude data 9Y, the controller 10 determines whether the change pattern of the rate of change in the altitude is a pattern due to a fall of the user or a pattern due to a downward movement of the elevator. For example, the controller 10 analyzes the change pattern of the rate in the altitude from the altitude data 9Y and, if the change pattern matches a detection pattern due to a fall of a user, determines that it is a pattern due to a fall of the user. For example, if the change pattern of the rate of change in the altitude does not match any patterns, the controller 10 may determine that it is a different pattern.

If it is determined that it is a pattern due to a fall of the user (Step S203, Yes), the controller 10 proceeds to Step S204. At Step S204, the controller 10 performs the emergency report process. For example, the controller 10 performs the emergency report process so as to make a phone call to a specific phone number via the communication unit 6. When the emergency report process is complete, the controller 10 terminates the steps of the process illustrated in FIG. 10.

If it is determined that it is not a pattern due to a fall of the user (Step S203, No), the controller 10 terminates the steps of the process illustrated in FIG. 10 without performing the emergency report process.

In this way, the smartphone 1 may determine whether a user has fallen or has moved downward by elevator in accordance with the pattern of the rate of change in the altitude, calculated based on the atmospheric pressure sensor 19, without checking the position of the device. As a result, the smartphone 1 may detect the occurrence of a fall accident on the basis of the atmospheric pressure even in a place where it is difficult to acquire the positional information on the device. Thus, if a fall accident occurs, the smartphone 1 may provide report control with good convenience.

With reference to FIG. 11, an explanation is given of the steps of the process for the smartphone 1's different control related to the time of fall. FIG. 11 is a flowchart that illustrates the steps of the process for an example of the smartphone 1's different control related to the time of fall. The steps of the process illustrated in FIG. 11 are performed when the controller 10 executes the control program 9A. The steps of the process illustrated in FIG. 11 are repeatedly performed.

As illustrated in FIG. 11, at Step S301, the controller 10 of the smartphone 1 calculates the altitude based on the atmospheric pressure. For example, the controller 10 applies the atmospheric pressure in the atmospheric pressure data 9X, detected by the atmospheric pressure sensor 19, to an altitude calculus equation to calculate the altitude and stores the calculation result in the altitude data 9Y of the storage 9.

At Step S302, the controller 10 calculates the amount of change in the altitude per predetermined time from the altitude data 9Y and stores the calculation result in the storage 9. At Step S303, the controller 10 determines whether the amount of change in the altitude exceeds the threshold. If it is determined that the amount of change in the altitude does not exceed the threshold (Step S303, No), the controller 10 terminates the steps of the process illustrated in FIG. 11.

If it is determined that the amount of change in the altitude exceeds the threshold (Step S303, Yes), the controller 10 proceeds to Step S304. At Step S304, the controller 10 acquires the positional information on the device. For example, the controller 10 acquires the latest positional information from the positional information stored in the position data 9W. The controller 10 may cause the GPS receiver 18 to detect the positional information so as to acquire the detected positional information.

At Step S305, the controller 10 determines whether the device is within the mountainous area 100. For example, the controller 10 determines that the device is within the mountainous area 100 if the present location of the device is within the area at the position that corresponds to the mountainous area 100.

If it is determined that the device is within the mountainous area 100 (Step S305, Yes), the controller 10 proceeds to Step S306. At Step S306, the controller 10 performs the emergency report process. For example, the controller 10 performs the emergency report process so as to make a phone call to a specific phone number via the communication unit 6. When the emergency report process is complete, the controller 10 terminates the steps of the process illustrated in FIG. 11.

If it is determined that the device is not within the mountainous area 100 (Step S305, No), the controller 10 terminates the steps of the process illustrated in FIG. 11 without performing the emergency report process.

In this way, if it is detected that the altitude changes due to a fall and if the device is located within the mountainous area 100, the smartphone 1 makes an emergency report. If it is detected that the altitude changes due to a fall and if the device is not located within the mountainous area 100, the smartphone 1 does not make any emergency report. As a result, the smartphone 1 may reduce the possibility of an improper emergency report on the occurrence of a decrease in the altitude due to a downward movement of the elevator when it is difficult to distinguish between a change in the altitude due to a fall and a change in the altitude due to a downward movement of the elevator.

In embodiments, an explanation is given of a case where the smartphone 1 determines whether it is a predetermined area on the basis of the present location detected by the GPS receiver 18; however, the embodiments are not limited thereto. Usually, the value of the atmospheric pressure is higher as the altitude is lower, and it is lower as the altitude is higher. For example, if the predetermined area is the mountainous area 100, the smartphone 1 may determine the mountainous area 100 when the detected atmospheric pressure (altitude) falls within the predetermined range of atmospheric pressure, within which there is a risk of fall.

In embodiments, an explanation is given of a case where, for the smartphone 1, the specific area is the mountainous area 100, the urban area 200, or the like; however, the embodiments are not limited thereto. For example, the specific area may be an area where an elevator is provided, an area where no elevator is provided, or the like.

In embodiments, the smartphone 1 is explained as an example of the mobile electronic device that includes the atmospheric pressure sensor 19; however, the mobile electronic device according to attached claims is not limited to the smartphone 1. The mobile electronic device according to attached claims may be a mobile electronic device other than the smartphone 1. Examples of the mobile electronic device include, but are not limited to, mobile phone, tablet, smartwatch, portable personal computer, head-mounted display, digital camera, media player, electronic book reader, navigator, and game machine.

Characteristic embodiments have been described to disclose the technology according to attached claims fully and clearly. However, attached claims do not need to be limited to embodiments, and they need to be configured so as to implement all the modifications and alternative configurations that may be created by a person skilled in the art within the range of fundamental matters that are described in this specification.

The invention claimed is:
1. A mobile electronic device, comprising:
   a position detector configured to detect a position of the device;
   an atmospheric pressure sensor configured to detect an atmospheric pressure; and
   a communication unit;
   a controller configured to determine a specific state if a decrease in an altitude is detected in accordance with the atmospheric pressure and if an amount of change in the altitude per predetermined time satisfies a determination condition,
wherein
   the controller is configured to make a determination as to whether the device is located within a specific area by using the position detector and change the determination condition in accordance with a result of the determination, and the controller is configured to
start to communicate with a different device by using the communication unit when the specific state is determined, and
not start to communicate with the different device by using the communication unit in response to determining that the device is located outside the specific area even if the specific state is determined.

2. The mobile electronic device according to claim 1, further comprising a storage configured to store positional information on the device, the positional information being detected by the position detector, wherein
when a change in the altitude is detected based on the atmospheric pressure sensor, the controller determines whether the device is located within the specific area in accordance with latest positional information in the storage.

3. The mobile electronic device according to claim 1, wherein if the specific area is a mountainous area and the determination condition is a threshold, the threshold is smaller when the device is located within the mountainous area than when the device is not located within the mountainous area.

4. The mobile electronic device according to claim 1, wherein if the specific area is an urban area and the determination condition is a threshold, the threshold is larger when the device is located within the urban area than when the device is not located within the urban area.

5. A mobile electronic device, comprising:
a position detector configured to identify a position of the device;
an atmospheric pressure sensor configured to measure an atmospheric pressure;
a communication unit; and
at least one controller, wherein
the at least one controller is configured
to determine value of reduced altitude per predetermined time based on the atmospheric pressure,
to determine a specific state if the value satisfies a determination condition, and
to change the determination condition if the position is located within a specific area,
the at least one controller is configured
to start to communicate with a different device by using the communication unit when the specific state is determined, and
to not start to communicate with the different device by using the communication unit in response to determining that the device is located outside the specific area even if the specific state is determined.

* * * * *